United States Patent
Dolechek

(10) Patent No.: US 6,536,450 B1
(45) Date of Patent: Mar. 25, 2003

(54) FLUID HEATING SYSTEM FOR PROCESSING SEMICONDUCTOR MATERIALS

(75) Inventor: Kert Dolechek, Kalispell, MT (US)

(73) Assignee: Semitool, Inc., Kalispell, MT (US)

( * ) Notice: Subject to any disclaimer, the term of this patent is extended or adjusted under 35 U.S.C. 154(b) by 0 days.

(21) Appl. No.: 09/372,849

(22) Filed: Aug. 12, 1999

Related U.S. Application Data

(60) Provisional application No. 60/142,684, filed on Jul. 6, 1999.

(51) Int. Cl.[7] ................................................. B08B 3/10
(52) U.S. Cl. ...................... 134/108; 134/105; 134/902; 165/163
(58) Field of Search ................................. 134/108, 105, 134/109, 902; 165/132, 163, 168

(56) References Cited

U.S. PATENT DOCUMENTS

| | | | | |
|---|---|---|---|---|
| 2,852,232 | A | * | 9/1958 | Marwell |
| 3,693,711 | A | * | 9/1972 | Zygiel |
| 3,703,086 | A | * | 11/1972 | Nijo |
| 3,706,343 | A | * | 12/1972 | Saiga et al. |
| 3,740,967 | A | * | 6/1973 | Huelle |
| 3,841,273 | A | * | 10/1974 | Finger et al. |
| 3,853,309 | A | * | 12/1974 | Widmer |
| 3,870,033 | A | * | 3/1975 | Faylor et al. |
| 4,071,075 | A | * | 1/1978 | Hinkle |
| 4,158,764 | A |   | 6/1979 | Yane |
| 4,161,980 | A | * | 7/1979 | Ruger |
| 4,335,870 | A | * | 6/1982 | Diener et al. |
| 4,343,988 | A | * | 8/1982 | Rolle et al. |
| 4,451,960 | A | * | 6/1984 | Molitor |
| 4,553,024 | A |   | 11/1985 | Findlay |
| 4,620,507 | A | * | 11/1986 | Saito et al. |
| 4,736,758 | A |   | 4/1988 | Kusuhara |
| 4,744,408 | A | * | 5/1988 | Pearson et al. |
| 4,747,450 | A | * | 5/1988 | Ikegame et al. |
| 4,813,396 | A | * | 3/1989 | Sargeant et al. |
| 4,826,538 | A |   | 5/1989 | Sanders et al. |
| 5,033,272 | A | * | 7/1991 | Yoshikawa et al. |
| 5,235,995 | A |   | 8/1993 | Bergman et al. |
| 5,285,845 | A | * | 2/1994 | Ostbo |
| 5,400,603 | A |   | 3/1995 | Bauer et al. |
| 5,419,393 | A | * | 5/1995 | Guy, III |
| 5,443,540 | A | * | 8/1995 | Kamikawa |
| 5,601,655 | A |   | 2/1997 | Bok et al. |
| 5,640,852 | A | * | 6/1997 | Atlas |
| 5,643,368 | A |   | 7/1997 | Nakashima |
| 5,772,783 | A | * | 6/1998 | Stucker |
| 5,899,077 | A | * | 5/1999 | Wright et al. |
| 5,941,083 | A | * | 8/1999 | Sada et al. |
| 5,979,474 | A |   | 11/1999 | Manako |
| 6,010,637 | A |   | 1/2000 | Lee et al. |
| 6,032,726 | A | * | 3/2000 | Wright et al. |
| 6,148,145 | A | * | 11/2000 | Kadotami et al. |
| 6,167,778 | B1 | * | 12/2000 | Kadotani |

OTHER PUBLICATIONS

European Patent Application 428,983 May 1991.*

* cited by examiner

Primary Examiner—Frankie L. Stinson
(74) Attorney, Agent, or Firm—Perkins Coie LLP

(57) ABSTRACT

A system for heating solvents in processing semiconductor wafers has a coiled solvent tube, a coiled cooling water tube, and electric heater elements, cast in place within an aluminum casting. The solvent flows through the solvent tube and is heated by conduction of heat through the casting. The solvent is safely isolated from the heating elements. Water is pumped through the cooling water tube, to cool the casting if solvent flow is interrupted, or if the measured casting temperature exceeds a predetermined set point temperature. Solvent temperature is maintained by controlling power to the heating elements based on the measured solvent temperature at the processing chamber.

9 Claims, 7 Drawing Sheets

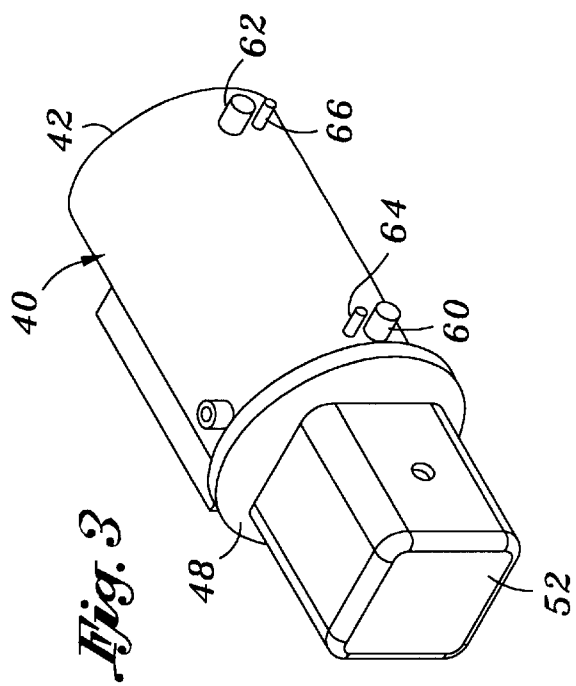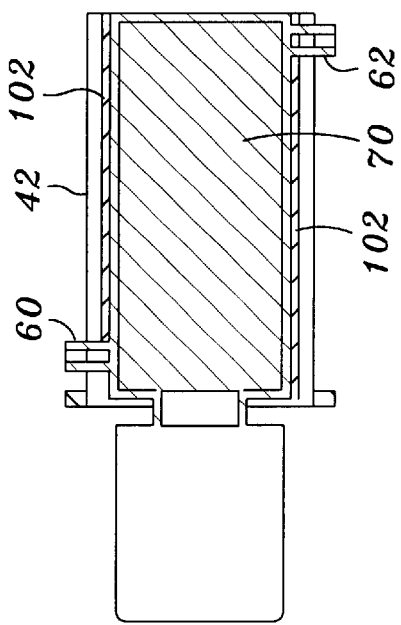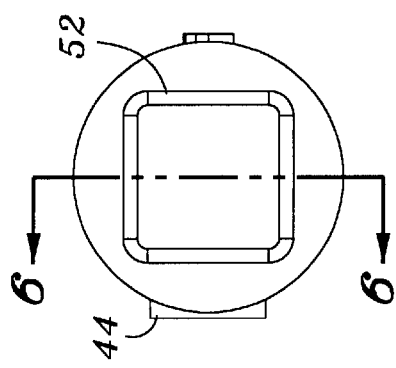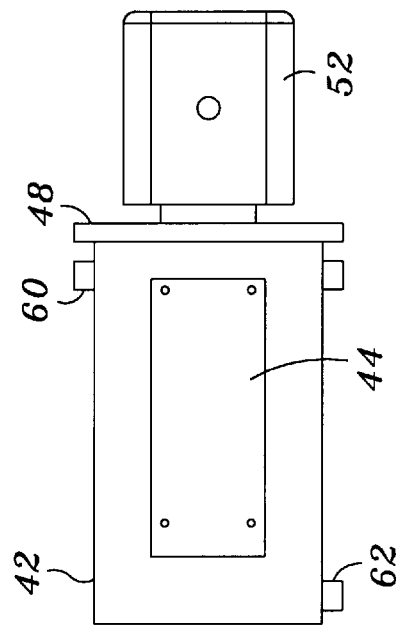

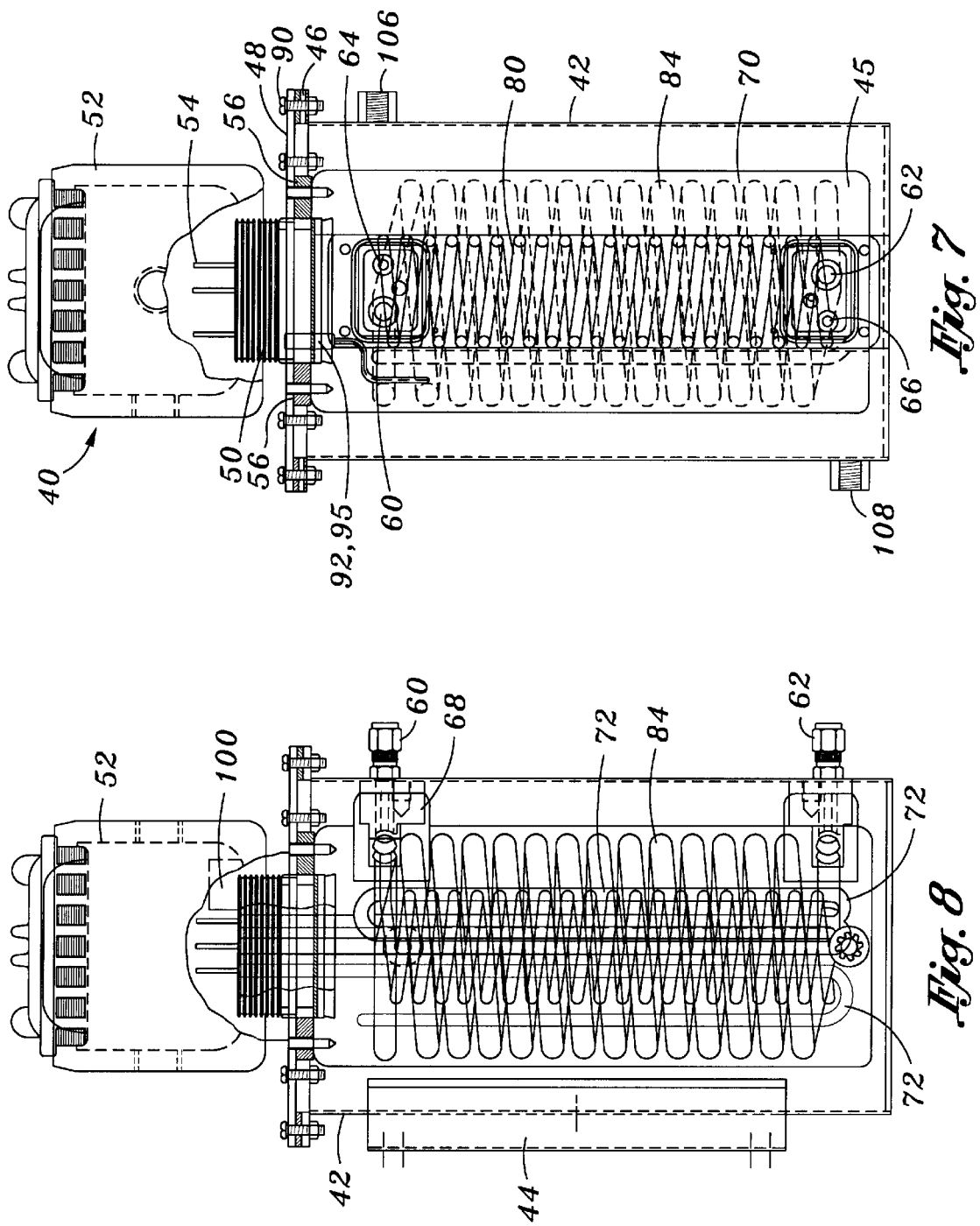

US 6,536,450 B1

FLUID HEATING SYSTEM FOR PROCESSING SEMICONDUCTOR MATERIALS

This application is a continuation-in-part of Ser. No. 60/142,684, filed Jul. 6, 1999, incorporated herein by reference.

The field of this invention is automated processing systems used for processing semiconductor wafers, hard disk media, substrates, and similar flat media requiring low levels of contamination. The invention also relates to heaters for solvents and other flammable fluids.

BACKGROUND OF THE INVENTION

Computers, televisions, telephones and other electronic products contain large numbers of electronic semiconductor devices. To produce electronic products, hundreds or thousands of semiconductor devices are manufactured in a very small space, using lithography techniques on semiconductor substrates, such as on silicon wafers. A large number of individual processing steps may be required to manufacture the semiconductor devices. Various machines and methods have been developed for these applications. For example U.S. Pat. No. 6,279,724, incorporated herein by reference, describes a system having processing chambers for processing and cleaning flat media (referred to below as "wafers").

In certain processing steps, it is advantageous, or necessary, to apply solvents to the wafers. To speed up and to better control the wafer processing, it is desirable to heat the solvent, and to closely control the temperature of the solvent which is applied to, e.g., sprayed onto, the wafers.

Heating solvents in a safe and reliable way presents unique challenges, because many solvents are combustible. Conventional heating techniques used for other types of fluids are generally unacceptable for heating solvents, due to the risk of igniting the solvent by a malfunctioning electrical heater or heater controller; or because they are unsuitable for the semiconductor manufacturing environment, which must be extremely clean and free of particles; or because they cannot meet the duty cycle requirements needed in semiconductor manufacturing. Quartz heater elements, which have been used to heat various liquids used in semiconductor manufacturing, are unacceptable for heating solvents, because of the risk that the brittle quartz will crack or break, exposing the combustible solvent to extreme temperatures and electrical contacts. On the other hand, tougher materials, such as stainless steel or Teflon, which can reduce or eliminate the risk of breakage of a heating element, and which are also compatible for use with solvents, are unfortunately poor conductors of heat. Accordingly, efficiently heating solvents has remained as a significant engineering challenge.

In the past, blanket heaters have been provided to heat a solvent in a storage tank to a specific set point temperature prior to delivery of the solvent to a wafer processing chamber. The tank blanket heaters are controlled to maintain that set point during processing. While this technique overcomes the difficulties presented by the volatile characteristics of solvents, it has certain, disadvantages. Initially, as the entire tank contents must be heated, the desired temperature changes occur slowly. In addition, the tank heaters are controlled based on the solvent temperature in the tank, resulting in significant delays in correcting the solvent temperature back, to the set point, during processing. The heat up time is also long, due to the conduction heating through the stainless steel tank walls, and due to the large mass of stationary solvent. As a result, the temperature of the solvent at the chamber cannot be closely controlled, resulting in poor processing uniformity, low strip/removal rates, and longer process times. Typical temperature drops are 4–8° C. from a set point of 75° C. In addition, the through put of the system, e.g., in the number of wafers processed per hour, is limited due to the time required for heating the solvent.

Accordingly, there is a need for an improved solvent heater, especially for use in processing semiconductor wafers.

SUMMARY OF THE INVENTION

In a first aspect of the invention, in a semiconductor processing machine, a heater for heating solvents includes a solvent tube, and a cooling tube, extending through a casting or other solid form. One or more heating elements extend into the casting. Heat from the heating element is/conducted through the casting or solid form, to heat solvent flowing through the solvent tube. As the solvent is isolated from the heating element via the solvent tube and solid material of the casting or solid form, the potential for igniting the solvent during heating is reduced or eliminated.

In a second aspect of the invention, the solvent tube and cooling tube are shaped into coils, with the cooling coil surrounded by the solvent coil. The cooling coil can rapidly cool the casting, if necessary, and can also help to control temperatures.

In a third aspect of the invention, the heating element has spaced apart legs which straddle the cooling coil.

In a fourth aspect of the invention, the solvent tube, cooling tube, and heating element are cast in place.

In a fifth aspect of the invention, the casting is enclosed within a container. The walls of the container are insulated from the casting. A purge gas is provided in the space between the insulation and the container walls, to provide an inert atmosphere around the casting.

In a sixth aspect of the invention, cool water is circulated through the cooling tube to rapidly cool the solvent to a temperature low enough to allow the used solvent to be drained from the semiconductor processing machine into the waste lines of a semiconductor manufacturing facility.

Other features and advantages will appear hereinafter.

BRIEF DESCRIPTION OF THE DRAWINGS

In the drawings, where the same reference number denotes the same element, throughout all of the views:

FIG. 3 is a simplified perspective view of the solvent heater shown in FIG. 2;

FIG. 4 is a side view thereof;

FIG. 5 is a top view thereof;

FIG. 6 is a simplified section view taken along line 6—6 of FIG. 5;

FIG. 7 is a front view showing the detailed construction of the solvent heater;

FIG. 8 is a side view thereof;

DETAILED DESCRIPTION OF THE DRAWINGS

Figure 1:
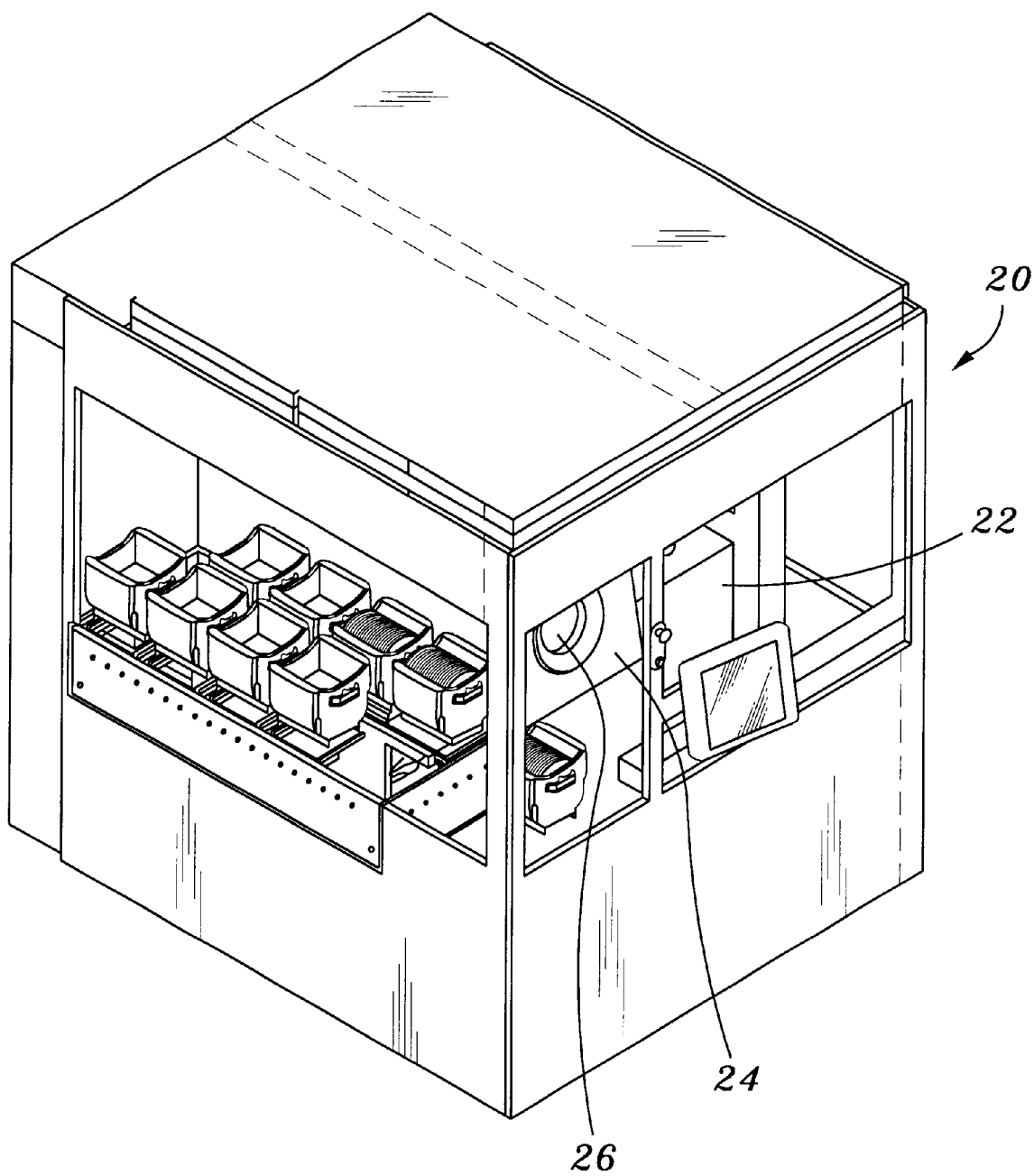
FIG. 1 is a perspective view of an automated semiconductor processing system.
Figure 2:
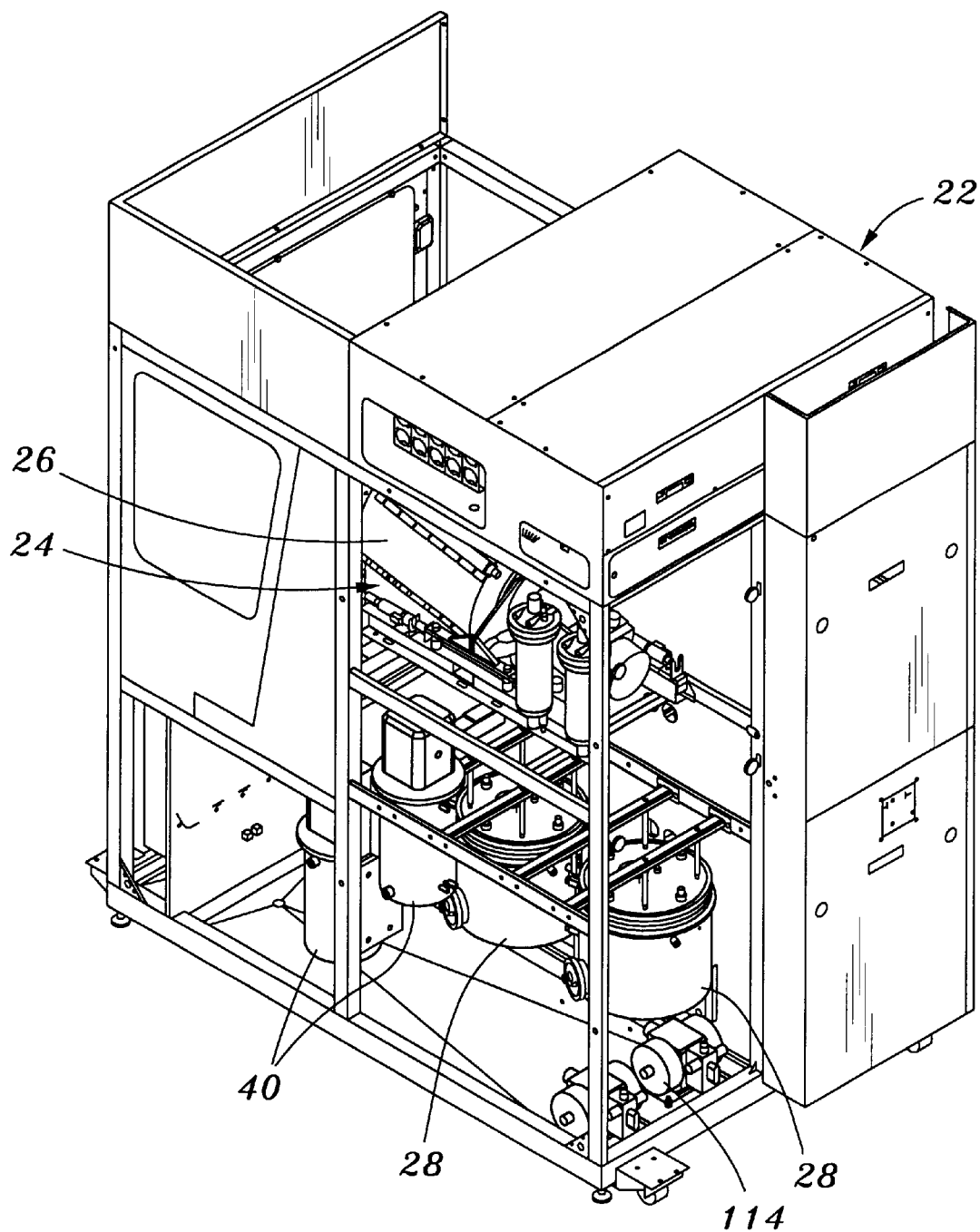
FIG. 2 is a perspective view of the processing unit shown in FIG. 1.
Figure 13:
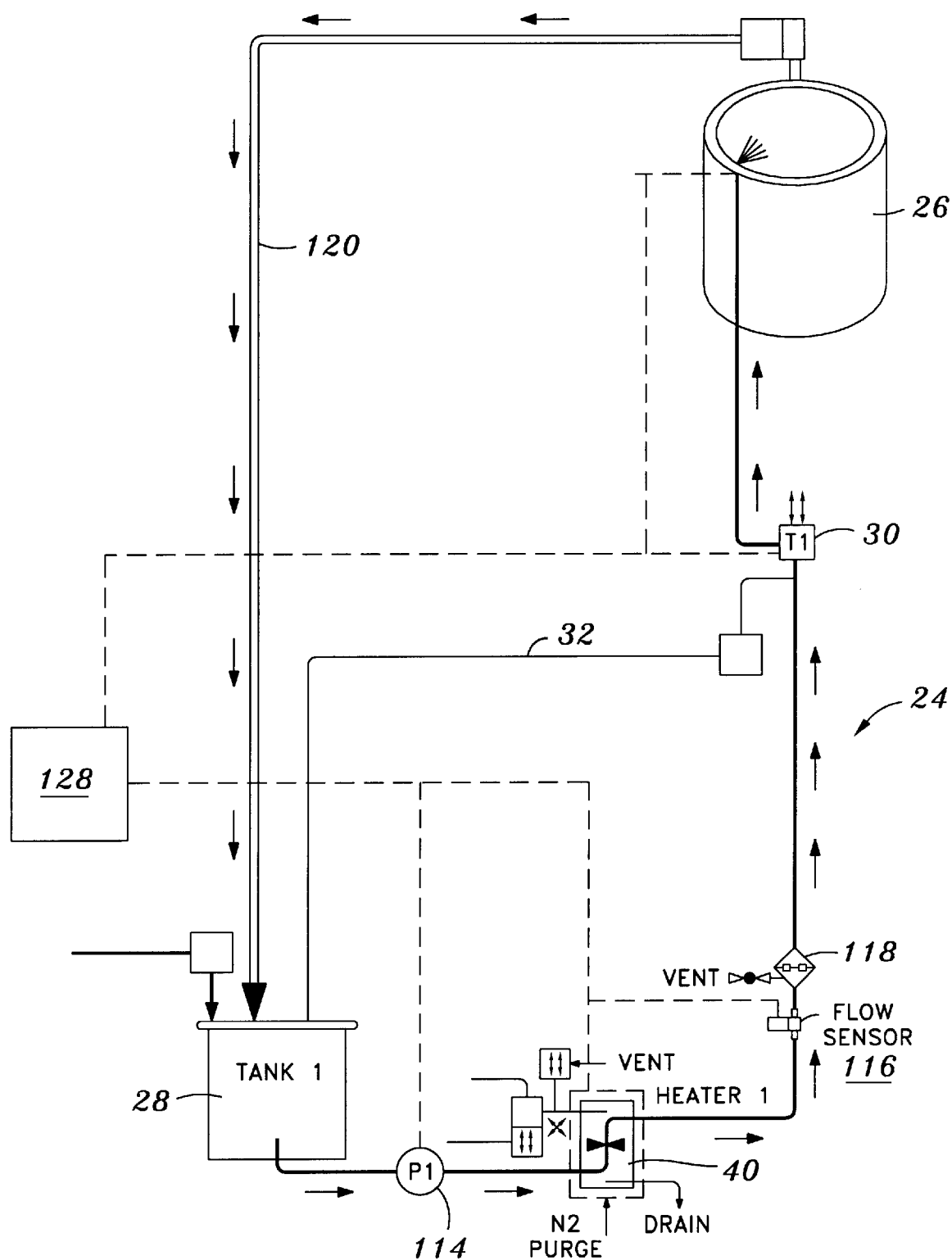
FIG. 13 is a schematic illustration of components of the processing unit shown in FIG. 2.

Turning now in detail to the drawings, as shown in FIG. 1, a wafer processing system 20 includes a processing unit 22 having two side by side centrifugal processors 24. Each centrifugal processor 24 has a chamber or bowl 26. Wafers are placed into a rotor within the chamber 26. The rotor spins the wafers, while solvents or other fluids are sprayed or applied to the wafers, during specific processing steps in the creation of semiconductor devices. The flat media processing system 20 is described in detail in U.S. Pat. No. 6,279,724, incorporated herein by reference. As shown in FIG. 2, a solvent heater 40 is included in the processing unit 22, to supply heated solvent to a chamber 26. Referring momentarily to FIG. 13, the solvent heater 40 is connected to the chamber 26 and to a solvent storage tank 28 with fluid connection lines.

Figure 10:
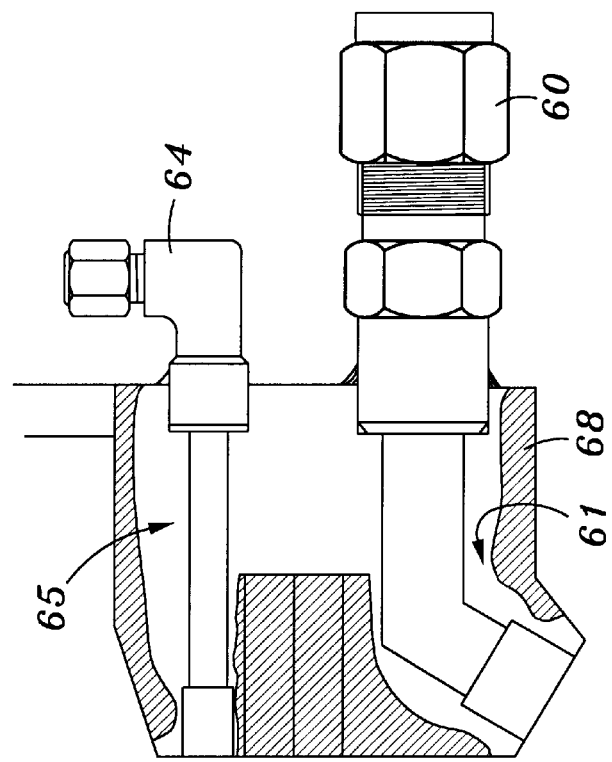
FIG. 10 is an enlarged detail showing certain of the features of FIG. 9.

Turning now to FIGS. 3–8, the solvent heater 40 includes a casting 70 (preferably aluminum alloy 319) or an equivalent substantially solid form of thermally conductive material. A solvent coil tube 84 and a cooling coil tube 80 are both embedded in, or cast in place, within the casting 70 or other solid form (hereinafter referred to as a casting). The solvent coil tube 84 has a solvent inlet 62 and solvent outlet 60 with pipe fittings, preferably compression (Swadgelok) fittings. Similarly, the cooling coil tube 80 has an inlet fitting 64 and an outlet fitting 66. In the embodiment shown, the solvent coil tube 84 is a ½ inch OD×0.049 wall×209 inches long (13 mm—1.2 mm×5300 mm) No. 316 stainless steel tube and the cooling coil tube 80 is a ¼ inch (6 mm) OD×153 inches (3890 mm) long No. 304 stainless steel tube. As shown in FIGS. 10 and: 11, the fittings are welded to bosses 68 which are also cast in place, at the top and bottom of the casting and they become part of the casting.

Figure 9:
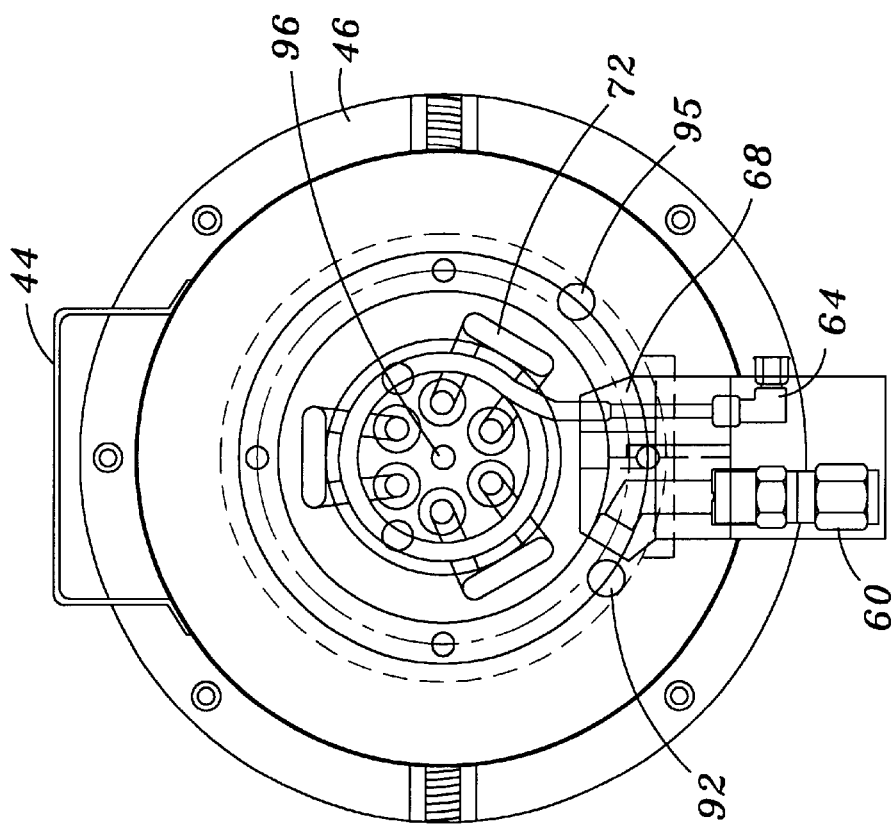
FIG. 9 is a plan view thereof (with various components removed for clarity of illustration)
Figure 12:
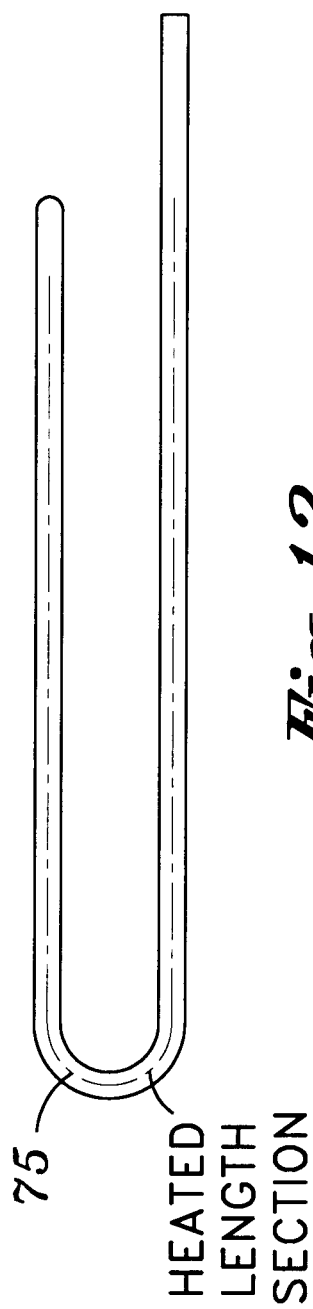
FIG. 12 is a side view thereof.
Figure 11:
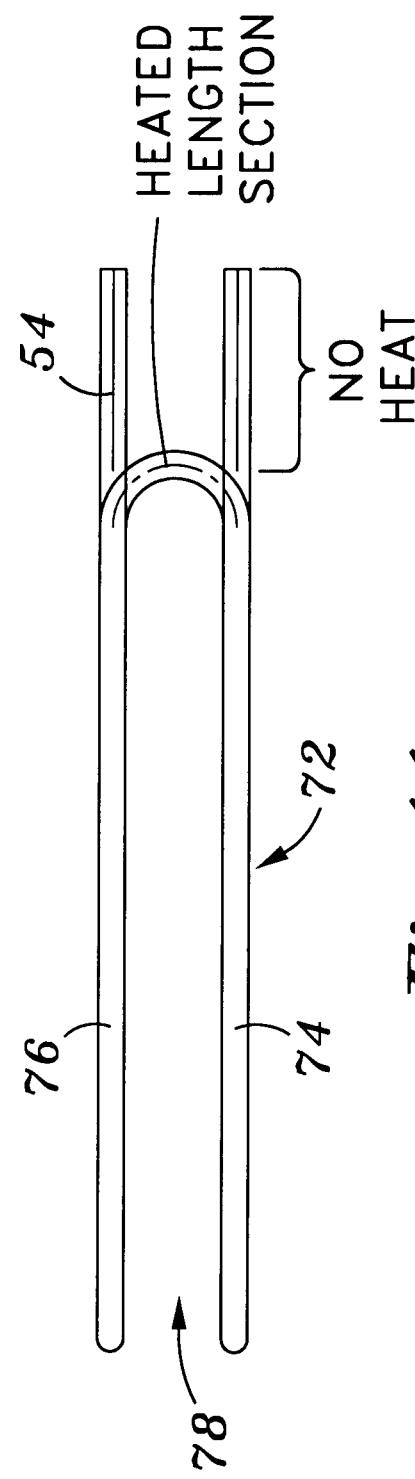
FIG. 11 is a top view of the heating elements showing in FIGS. 7–8.

The casting 70 is formed in a cylindrical shape. The solvent coil tube 84 is preferably concentric with, and surrounds the cooling coil tube 80. Three electrical resistance heaters 72 are equally, spaced apart within the casting 70, as shown in FIG. 9. Referring momentarily to FIGS. 11 and 12, each heater 72 has a first or inside leg 74 connecting to a second or outside leg 76 at an elbow 75. The first leg 74 is separated from the second leg 76 by a space 78.

Referring to FIGS. 7–8, the first leg 74 of each heater is inside of the cooling coil tube 80, while the second leg 76 of each heater 72 is outside of the cooling coil tube. Both legs 74 and 76 of the heaters 72 are within or surrounded by the solvent coil tube 84.

As best shown in FIGS. 7 and 8, the casting 70 is contained within a canister 42. The cylindrical canister 42 has an annular top rim 46. A round top plate 48 is secured to the top rim 46 by fasteners 90. An insulating gasket 56 separates the top plate 48 from the top rim 46. The casting 70 is attached to the top plate 48 via bolts 95. The casting 70 is accordingly suspended within the canister 42, such that the canister walls are separated from the casting by an air gap 104, on all sides (except at the top). A jacket of foam insulation 102 surrounds the casting 70, to reduce heat loss.

The solvent inlet and outlet fittings 62 and 60, and the cooling inlet and outlet fittings 64 and 66, pass through and seal externally against the canister 42 sidewalls. The canister 42 has removable cover plates 45, to allow installation of the casting into the canister.

Referring still to FIGS. 7 and 8, a stainless steel pipe section 50 is also cast in place and extends through the top plate 48. The pipe section is filled with cast aluminum. Three power leads 54 and a neutral lead from the heating elements 72 extend out of the pipe section 50 and extend into a NEMA box 52 threaded onto to the upper end of the pipe section 50. Electrical connections to provide power to the heating elements 72 are made within the NEMA box 52. In the embodiment shown, the heating elements are wired in a 3-phase Wye configuration, and operate at 380 V or 480 V, with a combined power of about 7.5 kw.

The canister 42 is sealed against its environment via the top plate 48 and the gasket 56, the cover plate 45, and the sealing surfaces on the fittings 60, 62, 64 and 68. A purge gas inlet 108 and a purge gas outlet 106 extend into the canister 42, so that the air gap 104 can be filled with another gas, such as nitrogen, which does not support combustion.

A first thermocouple 92 is located at the solvent outlet, to monitor the solvent tube wall temperature. A redundant thermal couple 95 is provided as a backup also at the solvent tube wall, for ruse if the first thermocouple fails. The thermocouples 92 and 95 are attached to outlet end of the solvent coil tube 84 and are cast in place. As shown in FIG. 9, another thermocouple 96 is cast in place near the heating elements 72, to monitor the heating elements temperature. The wire leads from the thermocouples 92, 95 and 96 extend out of the top of the casting 70, through the pipe section 50, and into the NEMA box 52.

A snap switch 100 is located within the NEMA enclosure 52 on the top surface of the casting 70, within the pipe section 50. The snap switch 100 senses the casting temperature and cuts power to the heaters 72, if a pre-determined set point is reached.

Turning to FIG. 13, blanket heaters 34 surround a solvent tank 28. A tank pump 114 pumps solvent from the tank 28 through a flow sensor 116 and into the heater 40. Solvent flows through the heater and through a filter 118 to a selection valve 30. The valve directs the solvent to either the chamber 26 or to a recirculation line 32. A return line 120 returns the solvent to the tank 28. As schematically shown in dashed lines in FIG. 13, a computer controller 128 is linked to the thermocouples 92, 94, 96; pump 114; flow sensor 116; valve 30; and to power controls for the heaters 34 and 40, and also to various other sensors and components. Nitrogen is continuously pumped through the canister via the purge inlet 108 and outlet 106. If solvent or solvent vapors collect in the canister 42 due to a leak, the nitrogen purging reduces any potential for ignition.

For each chamber 24 in the system 20, a minimum of one heated tank 28 is required to store the fluid solvent required for the processing. FIG. 13 conceptually shows a design for a single chamber 24.

In operation, a solvent fluid temperature set point (e.g., 70° C.) is entered into the controller or other circuitry as a fixed value during manufacture of the system 20. For safety and quality assurance reasons, this set point is limited to a maximum of e.g., 90° C. via software in the controller 38. At start up, power is applied to the blanket heaters 34. Solvent is pumped through the solvent coil tube 84. The flow of solvent, as detected by the flow sensor 116, enables power to the heating elements 72, which heat the casting. Temperatures are monitored via the thermocouples 92, 94 and 96. The solvent flow through the solvent coil tube 84 is preferably turbulent, to increase conductive heat transfer from the heating elements 72, through the casting, and into the solvent.

The valve 30 is positioned to direct the flowing solvent through the recirculation line 32 and back to the tank 28. When the solvent in the tank has reached the set point temperature, the processor 24 is ready to process wafers. At appropriate times during the process cycle, the valve 30 is positioned to direct solvent to the chamber 26. The solvent is sprayed onto wafers spinning in a rotor within the chamber 26. The solvent loses heat and cools down. The cooled solvent is then collected and flows under gravity through the return line 120 to the tank 28.

The power to the heating elements 72 is controlled based on the temperature of the solvent entering the chamber 26. This allows for rapid adjustments, so that the variations from the set point are greatly reduced.

Solvent is safely heated, as the solvent is separated from the heating elements 72 by the solid barrier of the cast material separating the heating elements and solvent coil tube 84. In the event of an over temperature condition, or if solvent stops flowing through the solvent coil tube 84, water is pumped through the cooling coil tube 80, to remove heat. The computer controller 38 linked to the water valve 110 opens valve 110 if a failure is detected. When the water valve 110 opens, water flows through the cooling tube 80, to cool the casting 70. The water then flows out to a drain.

With a solvent tank 28 having a volume of 15 liters, test data shows that the solvent temperature can be raised from 28° C. to 70° C. in 7–8 minutes, and from 28° C. to 87° C. in about 11 minutes, using a continuous recirculating flow rate of about 11 liters per minute. The temperature increase is about 5° C. per minute.

In many semiconductor fabrication facilities, waste line pipes cannot accept fluids warmer than about 50° C., due to the pipe material, and the chemically reactive characteristics of certain waste fluids, including solvents. Accordingly, fluids, such as solvents which are heated to e.g., 75° C., as is needed for efficient processing, cannot be released into waste lines, without first allowing them to cool down. Ordinarily, heated solvents are allowed to cool in a tank within a processing unit, such as the tank 28 in the processing unit 22. However, the processing unit 22 is then not useable during the cool down interval. Consequently, manufacture of semiconductors is slowed. The heater 40 allows this drawback to be minimized, by actively cooling the solvent, instead of storing the solvent in bulk and waiting for it to passively cool down in the tank. Specifically, to cool the solvent rapidly to a temperature acceptable for release into manufacturing facility waste lines, the solvent is circulated through the heater 40. However, the heating elements are turned off and cold water is circulated through the cooling coil. As a result, the used solvent is rapidly cooled and can be promptly released into the facility waste lines. The processing unit 22 is then available to process additional flat media.

Thus, a novel solvent heater for use with a semiconductor processing system safely heats solvents, decreases initial heat up time, better maintains target solvent temperature, and reduces recovery time. Various changes, modifications, and substitutions of equivalents may of course be made, without departing from the spirit and scope of the invention. The invention, therefore, should not be restricted, except by the following claims, and their equivalents.

We Claim:

1. A machine for processing semiconductor wafers, comprising:
   a combustible solvent supply;
   a cooling water supply;
   a processing chamber;
   a solvent heater including a solvent coil within the metal block, the solvent coil connecting with the solvent supply and the processing chamber;
   a cooling water coil within the metal block, the cooling water coil connecting with the cooling water supply; and
   at least one heating element in the metal block.

2. The machine of claim 1 further comprising a layer of insulation around the metal block.

3. The machine of claim 2 further comprising a container surrounding the metal block, wherein a purge gas space is provided between the layer of insulation and inner walls of the container.

4. The machine of claim 1 further comprising a container surrounding the metal block, wherein inner walls of the container are separated from the metal block by an air gap.

5. The machine of claim 1 wherein the solvent coil surrounds the cooling water coil.

6. The machine of claim 5 wherein the solvent coil is concentric with a longitudinal axis of the cooling water coil, and where a plurality of solvent heating elements are equally spaced apart around the longitudinal axis of the cooling water coil.

7. The machine of claim 1 wherein the solvent heating element includes a first leg within the cooling coil and a second leg outside of the cooling coil.

8. The machine of claim 1 wherein the metal block comprises a casting and the solvent heating element is cast in place within the metal casting.

9. A machine for processing semiconductor wafers using a combustible solvent, comprising:
   a combustible solvent supply;
   a cooling water supply;
   a processing chamber;
   a combustible solvent heater having a block of metal;
   a solvent coil extending through the block of metal and connecting with the solvent supply and an outlet connecting with the processing chamber;
   a cooling coil extending through the block of metal and having an inlet connecting with the cooling water supply;
   at least one heating element in the block of metal;
   a container around the block metal with a purge gas space between the container and the block of metal; and
   a purge gas supply connecting with the purge gas space.

* * * * *